United States Patent
Yuan et al.

(10) Patent No.: US 10,342,853 B2
(45) Date of Patent: Jul. 9, 2019

(54) LEPTIN ACTIVE PEPTIDE HAVING D HELIX REGION MUTATIONS, CODING GENE THEREOF, AND APPLICATION THEREOF

(71) Applicant: SHANGHAI YUANXIN BIOCHEMICAL SCIENCE AND TECHNOLOGY CO. LTD., Shanghai (CN)

(72) Inventors: Lihong Yuan, Guangzhou (CN); Jiahai Lu, Guangzhou (CN); Benfu Lin, Guangzhou (CN)

(73) Assignee: SHANGHAI YUANXIN BIOCHEMICAL SCIENCE AND TECHNOLOGY CO. LTD., Shanghai (CN)

( * ) Notice: Subject to any disclaimer, the term of this patent is extended or adjusted under 35 U.S.C. 154(b) by 0 days.

(21) Appl. No.: 15/805,071

(22) Filed: Nov. 6, 2017

(65) Prior Publication Data

US 2018/0050093 A1    Feb. 22, 2018

Related U.S. Application Data

(63) Continuation of application No. PCT/CN2015/088535, filed on Aug. 31, 2015.

(30) Foreign Application Priority Data

May 6, 2015 (CN) .......................... 2015 1 0228121

(51) Int. Cl.
*C07K 14/575* (2006.01)
*A61K 38/22* (2006.01)
*A61K 48/00* (2006.01)
*A61K 38/00* (2006.01)

(52) U.S. Cl.
CPC ...... *A61K 38/2264* (2013.01); *C07K 14/5759* (2013.01); *A01K 2217/05* (2013.01); *A61K 38/00* (2013.01); *A61K 48/00* (2013.01)

(58) Field of Classification Search
CPC .. C07K 14/575; C07K 14/5759; A61K 38/22; A61K 38/2264
See application file for complete search history.

(56) References Cited

U.S. PATENT DOCUMENTS

| | | |
|---|---|---|
| 6,399,745 B1 | 6/2002 | Ertl et al. |
| 7,470,669 B2 * | 12/2008 | Yen .......................... A61K 8/64 514/1.1 |
| 2006/0154859 A1 * | 7/2006 | Gertler ................ C07K 14/5759 530/300 |
| 2012/0149636 A1 * | 6/2012 | Kraynov ............ C07K 14/5759 514/5.8 |
| 2013/0133089 A1 * | 5/2013 | Gertler ................... A61K 38/22 800/3 |

FOREIGN PATENT DOCUMENTS

| | | |
|---|---|---|
| CN | 104829708 A | 8/2015 |
| WO | WO-9720933 A2 * | 12/1996 |
| WO | 0166593 A1 | 9/2001 |

OTHER PUBLICATIONS

Bork, A. Powers and pitfalls in sequence analysis: the 70% hurdle. Genome Res 10: 398-400, 2000.*
Bork et al. Go hunting in sequence databases but watch out for the traps. Trends in Genetics. 12(10): 425-427, 1996.*
Brenner, S.E. Errors in genome function. Trends in Genetics 15(4): 132-133, 1999.*
Denver et al. Evolution of leptin structure and function. Neuroendocrinol 94: 21-38, 2011.*
Doerks et al. Protein annotation: detective work for function prediction. Trends in Genetics 14(6): 248-250, 1998.*
Ngo et al. Computational complexity, protein structure prediction, and the Levinthal paradox. The Protein Folding Problem and Tertiary Structure Prediction, pp. 492-495, 1994.*
Otvos et al. Development of a pharmacologically improved peptide agonist of the leptin receptor. Biochim Biophys Acta 1783: 1745-1754, 2008.*
Peelman et al. Insights into signaling assemblies of the leptin receptor. J Endocrinol 223: T9-T23, 2014.*
Peelman et al. Mapping of the leptin binding sites and design of a leptin antagonist. J Biol Chem 279(39): 41038-41046, 2004.*
Skolnick et al. From genes to protein structure and function: novel applications of computational approaches in the genomic era. Trends in Biotech 18(1): 34-39, 2000.*
Smith et al. The challenges of genome sequence annotation or "The devil is in the details". Nature Biotech 15: 1222-1223, 1997.*
Tokuriki et al. Stability effects of mutations and protein evolvability. Curr Opin Structural Biol 19: 596-604, 2009.*
Wells. J.A. Additivity of mutational effects in proteins. Biochemistry 29 (37): 8509-8517, 1990.*
International Search Report of PCT/CN2015/088535 dated Feb. 5, 2016.

\* cited by examiner

*Primary Examiner* — Bridget E Bunner
(74) *Attorney, Agent, or Firm* — Erson IP (Nelson IP)

(57) ABSTRACT

A leptin active peptide having helix D region mutation, a coding gene thereof, and an application thereof are provided in the present invention. An amino acid sequence of the leptin active peptide having helix D region mutation is shown in SEQ ID NO.1.

1 Claim, 2 Drawing Sheets
Specification includes a Sequence Listing.

SEQUENCE LISTING

```
<160> NUMBER OF SEQ ID NOS: 1

<210> SEQ ID NO 1
<211> LENGTH: 24
<212> TYPE: PRT
<213> ORGANISM: Artificial Sequence
<220> FEATURE:
<223> OTHER INFORMATION: An amino acid sequence of the leptin active
      peptide having helix D region mutation
```

-continued

```
<400> SEQUENCE: 1

Ser Thr Glu Val Val Ala Leu Asp Gly Leu Gln Gly Ser Leu Gln Thr
1               5                   10                  15

Met Leu Leu Gln Leu Glu Tyr Ser
            20
```

LEPTIN ACTIVE PEPTIDE HAVING D HELIX REGION MUTATIONS, CODING GENE THEREOF, AND APPLICATION THEREOF

CROSS-REFERENCE TO RELATED APPLICATIONS

This application is a continuation of International Patent Application No. PCT/CN2015/088535 with a filing date of Aug. 31, 2015, designating the United States, now pending, and further claims priority to Chinese Patent Application No. 201510228121.6 with a filing date of May 6, 2015. The content of the aforementioned applications, including any intervening amendments thereto, are incorporated herein by reference.

FIELD OF THE INVENTION

The present invention belongs to the fields of biochemistry and molecular biology, and particularly relates to a leptin active peptide having helix D region mutation, a coding gene thereof, and an application thereof.

BACKGROUND OF THE INVENTION

Obesity is one of the worst enemies of human health. Obesity is an independent disease as well as a pathogenic cause of type II diabetes, cardiovascular diseases, hypertension, cerebral apoplexy and multiple cancers, is listed as one of top ten threats causing disease burdens by World Health Organization, and is a global issue that cannot be ignored. It is reported that about 18 million people die from cardiovascular and cerebrovascular diseases caused by diabetes and hypertension every year in the world, while the obesity is a key pathogenic factor of the diabetes and hypertension. The obesity seriously endangers human health and causes huge losses to the society. It is reported in 2003 that, expenditure for chronic diseases such as the obesity, the diabetes and the like reaches RMB 1200 billion in China and accounts for 10.3% of GDP. An increasing rate of the expenditure is higher than an increasing rate of Gross National Product (GNP). At present, domestic weight loss market needs are very wide. Consumption amount of weight loss products reaches RMB 60 billion in 2010, while losses caused by diseases, such as the diabetes, cardiovascular diseases and the like, directly or indirectly related to the obesity are beyond calculation. At present, although drugs for treating the obesity and the diabetes, i.e., fenofibrate and rosiglitazone, can achieve effects of reducing blood fat and blood sugar, serious side effects, such as insulin resistance, "mutagenesis, carcinogenesis and teratogenesis" effects and the like, may be caused to a human body when the drugs are taken for a long time. Therefore, safe, efficient and cheap novel drugs are urgently needed in clinical treatment of the obesity and the diabetes.

Leptin is a hormone substance secreted by adipose tissue. Six Leptin receptors participate in fat metabolism and appetite regulation of the organism. At the beginning of this century, the leptin is discovered and successfully tested on a mouse model suffering from the obesity. A stir in scientific circles is created. It is forecast that biotechnology finds a novel weight loss drug for hundreds of millions of obese patients around the world. In 1999, through study, scientists have found that polypeptide fragments of 116th-130th amino acid tissues of a human-derived leptin protein have obvious lipid degradation activities. Later, American scientists first carried out the first leptin protein experiment on human being. However, in 73 tested obese patients, most of the patients do not have an obvious weight loss effect, and only 2 patients lose weight by 35 pounds within 24 weeks, which indicates that an ideal weight loss effect is difficult to he achieved by using a wild type human-derived leptin protein.

SUMMARY OF THE INVENTION

A first objective of the present invention is to provide a leptin active peptide having helix D region mutation with excellent adipocyte-degrading activity.

An amino acid sequence of the leptin active peptide having helix D region mutation in the present invention is shown in SEQ ID NO.1.

A second objective of the present invention is to provide a coding gene of the leptin active peptide having helix D region mutation.

A third objective of the present invention is to provide an application of the leptin active peptide having helix D region mutation in preparation of adipocyte-degrading drugs, weight loss drugs or hypoglycemic drugs.

In the present invention, an amino acid sequence of human-derived leptin is modified for increasing lipid degradation efficiency. The leptin active peptide having helix D region mutation is synthesized by utilizing chemical methods respectively, and an influence of a protein space structure on an activity of the leptin is reduced as much as possible, thereby enhancing targeting and degrading effects on adipocytes. Practical results indicate that the adipocyte-degrading activity of the leptin active peptide having helix D region mutation in the invention is obviously better than that of positive control-human-derived leptin protein (H-LEP) and a commercially available drug rosiglitazone (Ros); the lipid-lowering activity of the leptin active peptide has obvious concentration dependence and dependence in a cell differentiation period; the leptin active peptide has obvious cell lysis effects at three stages, i.e., a preadipocytes stage, a differentiation stage (D0-D2) and a mature adipocyte stage (D9); and effects of the leptin active peptide are obviously better than two positive controls (H-LEP and rosiglitazone), thereby providing a candidate target for developing novel, efficient and cheap weight loss and blood-sugar reducing drugs.

DETAILED DESCRIPTION OF THE EMBODIMENTS

Figure 1:
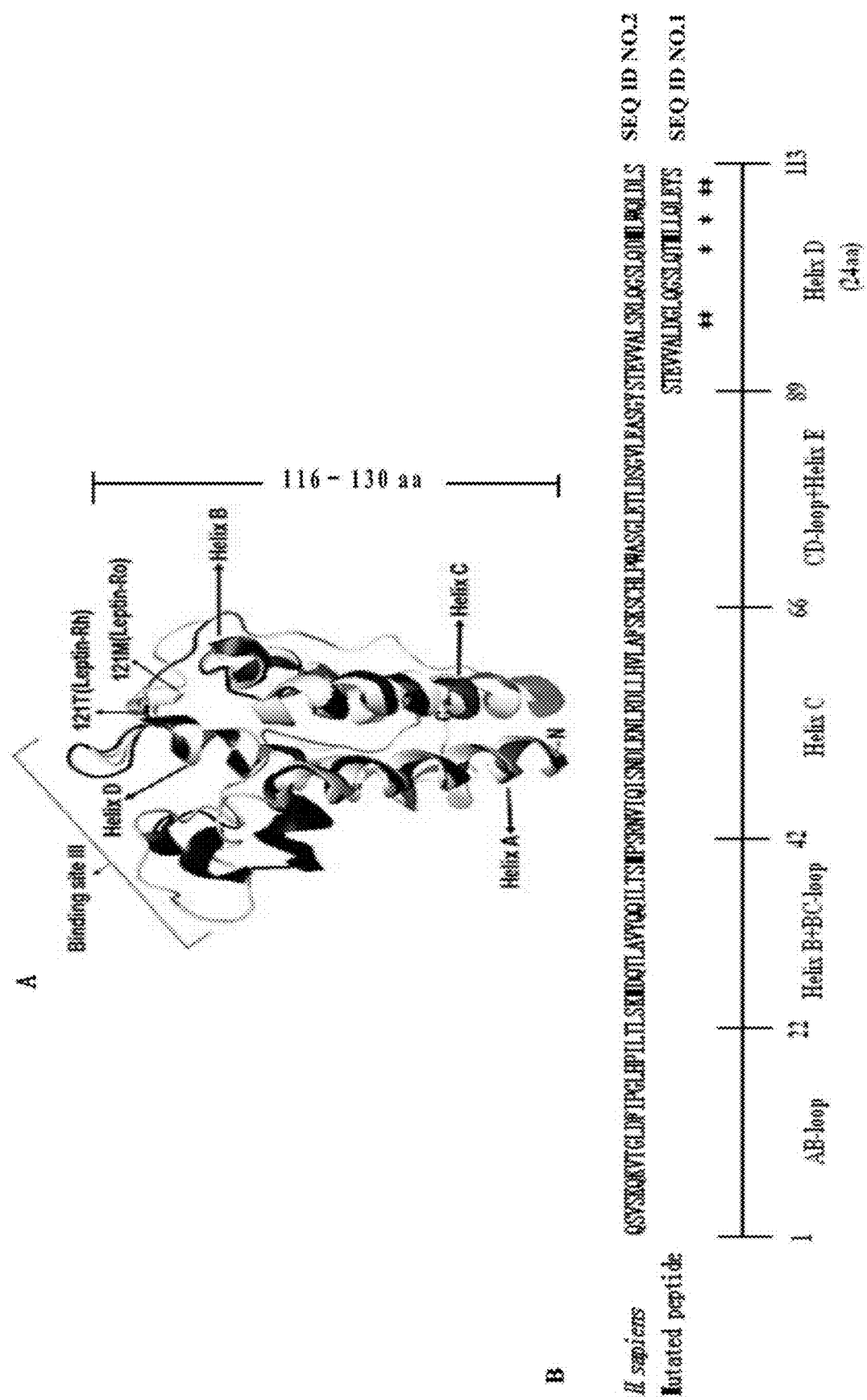
FIG. 1 is a design of a leptin active peptide having helix D region mutation; A: a three-dimensional structural diagram simulated and constructed by taking a human-derived Leptin sequence as a template; B: amino acid sequence alignment and function division of No. 3 exon of the human-derived Leptin (upper) and the leptin active peptide having helix D region mutation (lower). *: mutation site.

Embodiments below are further descriptions of the present invention, rather than limitations to the present invention.

Embodiment 1

Material and Method 1.1 Design and Synthesis of Leptin Active Peptide Having Helix D Region Mutation A leptin active peptide having helix D region mutation is designed in a functional region thereof according to hydrophilic/hydrophobic property change conditions of mutation sites by taking an amino acid sequence of human-derived leptin as a template, and the ammo acid sequence is STEVVALDGLQGSLQTMLLQLEYS (specifically shown as SEQ ID NO. 1). The leptin active peptide having helix D region mutation is synthesized by Shanghai Sangon Biotech Co., Ltd. Through HPLC detection, a concentration of the chemosynthetic leptin active peptide having helix D region mutation is greater than 95.51%, and a requirement for subsequent activity analysis is met. The accuracy of the synthesized leptin active peptide having helix D region mutation is detected by mass spectrometry, and the amino acid sequence of the leptin active peptide is confirmed as STEVVALDGLQGSLQTMLLQLEYS (specifically shown as SEQ ID NO. 1).

1.2 In-Vitro Lipid-Lowering Activity Analysis of the Leptin Active Peptide

Lipid degradation activity of the synthesized leptin active peptide having helix D region mutation is analyzed on a cellular level by taking a 3T3-L1 preadipocyte line as a model. Specific operations are as follows:

1.2.1 Experimental Design (1) Grouping:

a: preadipocytes;

b: an early differentiation stage D0-D2 (0-2nd day of induced differentiation); and c: a mature adipocyte stage D9 (the 9th day of induced differentiation);

(2) Leptin Peptide and Control a. leptin active peptide having helix D region mutation (PEP-D): diluted to $10^{-3}$M with purified water and preserved at −20 degree C. for later use. After an experiment is started, working concentrations have 3 concentration gradients, that is, $10^{-6}$M, $10^{-9}$M and $10^{-11}$M;

b. positive control. I: H-LEP, recombinant human-derived leptin protein (10221-HNAE, Beijing Sino Biological Inc.), diluted to $10^{-6}$M with purified water and preserved at −20 degree C. for later use. After an experiment is started, the working concentration is $10^{-9}$M;

c. positive control 2: Ros (Rosiglitazone, 82408, Sigma), diluted to a stock solution with a concentration of 2518 μM with DMSO and preserved at −20 degree C. for later use. After an experiment is started, the stock solution is diluted to a working solution of 0.5 μM with cell culture fluid;

d. negative control (Control): equivalent quantity of PBS (3) Cell Differentiation Induced Liquid a. cell differentiation induced liquid I: a complete medium containing 0.5 μM IBMX (3-Isobutyl-1-methylxanthine, 15879, Sigma), 1 μM dexamethasone (dexamethasone, D4902, Sigma) and 167 nM insulin (insulin, 15500, Sigma);

b. cell differentiation induced liquid II; a complete medium containing 167 nM insulin (insulin, 15500, Sigma).

1.2.2 3T3-L Preadipocyte Culture (1) A complete culture solution; DMEM culture medium of 10% FBS (fetal calf serum)-DMEM 45 ml+FBS 5 ml+double-antibody 0.5-0.8 ml (DMEM, Hyclone SH30243.01B500 ml high glucose, containing L-glutamine, sodium pyruvate, Fetal Bovine Serum, Invitrogen 10091-148, Penicillin-Streptomycin, Invitrogen 15140-122 1.00.times.).

(2) Passage: sucking old liquid, washing twice with calcium-magnesium-free PBS, adding 0.5 ml/T25 0.25% pancreatin, digesting for about 2 min (when most of cells float), and stopping digestion with complete culture solution; directly inoculating in a novel 25 cm² culture bottle (T25) according to a ratio 1:3 without centrifuging; and changing the liquid after 3-4 hours, and performing passage in time while growing by about 70%.

1.23 Induced Differentiation of 313-L1 Preadipocytes into Mature Adipocytes (1) Inoculating 3T3-L1 preadipocytes in corning cell bind 96-well plates (totally inoculated with 3 plates, respectively plate a, plate b and plate c), wherein the inoculation density is 4500 cells/well; and marking, and standing and culturing at 37 degree C. in a 5% $CO_2$ incubator. Each sample of each plate is operated repeatedly for 3 times, and the whole experiment is repeated for 3 times;

(2) Continuously culturing for 48 hours after the cells are merged to 100% (enabling the cells to exit from a growth cycle, and starting induced differentiation); and (3) After the cells exit from the growth cycle, a. preadipocytes:

i, taking out the plate a; respectively adding different amounts of leptin active peptide having helix D region mutation (PEP-D) to enable the working concentrations to be respectively 3 concentration gradients, that is, $10^{-6}$M, $10^{-9}$M and $10^{-11}$M; setting 2 positive controls, a negative control (PBS) and a blank control (3 repeated holes are set for each sample), and continuously standing and culturing at 37 degree C. in the 5% CO2 incubator.

ii, when culturing to 45 hours (that is, 3 hours before the end of drug treatment), taking out the plate a, and measuring MTT (preadipocytes). Specific operations: adding 20 μL of 5 mg/mL of MTT solution into each well, continuously standing and culturing at 37 degree C. in the 5% $CO_2$ incubator for 3 hours, sucking and discarding the culture solution in the wells, adding 150 μL of DMSO into each well, horizontally shaking for 10 min, detecting a light absorption value at 492 nm by a microplate reader, and drawing a growth curve;

b, the early differentiation stage (D0-D2):

i, taking out the plate b; adding the differentiation induced liquid I (D0); respectively adding the leptin active peptide having helix D region mutation (PEP-D); setting 2 positive controls, a negative control (PBS) and a blank control (3 repeated holes are set for each sample), and continuously standing and culturing at 37 degree C. in the 5% $CO_2$ incubator.

ii, when culturing to 45 hours (that is, 3 hours before the end of drug treatment), taking out the plate b, and measuring MTT (at the early differentiation stage, D0-D2). Specific operations: adding 20 μL, of 5 mg/mL of MTT solution into each well; continuously standing and culturing at 37 degree C. in the 5% $CO_2$ incubator for 3 hours; sucking and discarding the culture solution in the wells; adding 150 μL of DMSO into each well; horizontally shaking for 10 min; detecting a light absorption value at 492 nm by the microplate reader; and drawing a growth curve;

c. the mature adipocyte stage (D9):

i, taking out the plate c; adding the differentiation induced liquid I (D0) into each well; and continuously standing and culturing at 37 degree C. in the 5% $CO_2$ incubator for 48 hours;

ii, after treating with the differentiation induced liquid I (D2) for 48 hours, taking out the plate c, adding the differentiation induced liquid II into each well, and continuously standing and culturing at 37 degree C. in the 5% $CO_2$ incubator;

iii, after treating with the differentiation induced liquid II (D4) for 48 hours, taking out the plate c and replacing with a normal complete medium, and continuously standing and culturing at 37 degree C. in the 5% $CO_2$ incubator;

vi, after culturing for 48 hours (D6) after replacing with the normal complete medium, taking out the plate c to replace the liquid, and continuously standing and culturing at 37 degree C. in the 5% $CO_2$ incubator for 24 hours;

v, culturing to D7 (the $7^{th}$ day); taking out the plate c to replace the liquid (a complete medium); respectively adding the leptin active peptide having helix D region mutation (PEP-D); setting 2 positive controls, a negative control (PBS) and a blank control (3 repeated holes are set for each sample); and continuously standing and culturing at 37 degree C. in the 5% $CO_2$ incubator for 48 hours; and iv, when treating with drugs for 45 hour (that is, 3 hours before the end of drug treatment), taking out the plate c, and measuring MTT (mature adipocyte stage, D9). Specific operations: adding 20 μL of 5 mg/mL of MTT solution into each well; continuously standing and culturing at 37 degree C. in the 5% CO2 incubator for 3 hours; sucking and discarding the culture solution in the wells; adding 150 μL of DMSO into each well; horizontally shaking for 10 min; detecting a light absorption value at 492 nm by the microplate reader, and drawing a growth curve.

1.2.4 Statistical Analysis

The MTT detection data is subjected to one-way analysis of variance (ANOVA) by using SPSS17.0 software.

2. Results 2.1 Design and Synthesis of Leptin Active Peptide Having Helix D Region Mutation The Leptin active peptide having helix D region mutation is designed and has 6 ammo acid mutation sites compared with human-derived leptin. A peptide sequence is as follows: STEVVALDGLQGSLQTMLLQLEYS (shown in SEQ ID NO. 1, molecular weight: 2595.05; see FIG. 1 for details). Through HPLC detection, a concentration of the chemosynthetic leptin active peptide is greater than 95.51%, and a requirement for subsequent activity analysis is met.

2.2 MTT Lipid-Lowering Activity Analysis

Figure 2:
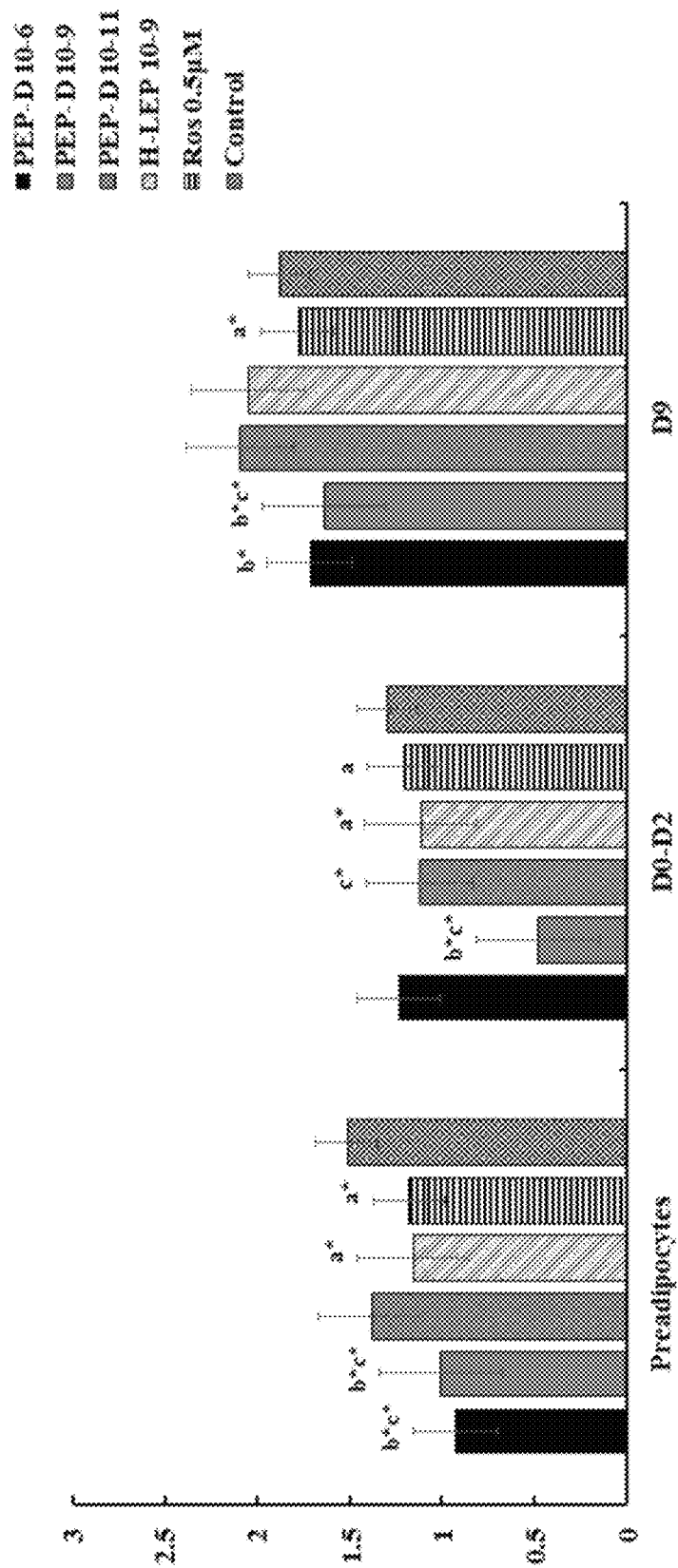
FIG. 2 shows activity analysis of a leptin active peptide having helix D region mutation; Lip-lowering activity analysis of 3T3-L1 preadipocytes (MTT detection); PEP-D: the leptin active peptide having helix D region mutation, as well as $10^{-6}$, $10^{-9}$ and $10^{-11}$ after the PEP-D respectively refer to concentrations, such as $10^{-6}$M, $10^{-9}$M and $10^{-11}$M, of the leptin active peptide having helix D region mutation; H-LEP: human-derived leptin protein (positive control), and $10^{-9}$ refers to $10^{-9}$M; Ros: rosiglitazone (positive control 2); Control: negative control. Preadipocytes: induced preadipocytes stage; D0-D2: 0-2nd day of induced differentiation (an early stage of differentiation); D9: the 9th day of induced differentiation (a mature adipocyte stage). Statistical analysis: a, positive control (H-LEP/Ros) vs. negative control (Control), adipocyte lysis activity of the positive control is obviously better than that of the negative control, P<0.05; b, PEP-D vs. H-LEP, adipocyte lysis activity of the PEP-D is obviously better than that of the H-LEP, P<0.05; c. PEP-D vs. Ros, and adipocyte lysis activity of the PEP-D is obviously better than that of the Ros, P<0.05; and *, p<0.01.

Cell activity analysis results show that the adipocyte-degrading activity of the synthesized leptin active peptide having helix D region mutation is obviously better than that of positive control-human-derived leptin protein (H-LEP) and a commercially available drug rosiglitazone (Ros) at three cell differentiation stages (that is, the preadipocytes stage, the early differentiation stage and the mature adipocyte stage), and the lipid-lowering activity of the leptin active peptide having helix D region mutation has obvious concentration dependence. On a whole, the concentration $10^{-9}$M has an optimal lipid-lowering effect (FIG. 2).

SEQ ID NO. 1

| Sequence table | |
|---|---|
| <160> | 1 |
| <210> | 1 |
| <211> | 24 |
| <212> | PRT |
| <213> | Artificial sequence |
| <400> | 1 |
| Ser Thr Gln Val Val Ala Len Asp Gly Leu Gln Gly Ser Leu Gln<br>1                    5                              10                        15<br>Thr Met Leu Leu Gln Leu Glu Tyr Ser<br>                  20                 24 | |

We claim:
1. A leptin active peptide having helix D region mutations, wherein said peptide comprises the amino acid sequence of SEQ ID NO:1.

* * * * *